(12) United States Patent
Hartzell et al.

(10) Patent No.: US 8,236,245 B2
(45) Date of Patent: *Aug. 7, 2012

(54) MICRO-PIXELATED FLUID-ASSAY PRECURSOR STRUCTURE

(75) Inventors: John W. Hartzell, Camas, WA (US); Pooran Chandra Joshi, Vancouver, WA (US); Paul J. Schuele, Washougal, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 627 days.

This patent is subject to a terminal disclaimer.

(21) Appl. No.: 11/827,335

(22) Filed: Jul. 10, 2007

(65) Prior Publication Data

US 2008/0085214 A1 Apr. 10, 2008

Related U.S. Application Data

(60) Provisional application No. 60/849,875, filed on Oct. 6, 2006.

(51) Int. Cl.
*G01N 3/00* (2006.01)
(52) U.S. Cl. ....... 422/82.05; 422/62; 422/129; 422/400; 385/12; 385/129; 356/317; 356/440; 435/287.1; 435/288.7; 506/9
(58) Field of Classification Search .................. None
See application file for complete search history.

(56) References Cited

U.S. PATENT DOCUMENTS

| | | | |
|---|---|---|---|
| 5,143,854 A | 9/1992 | Pirrung et al. | |
| 5,514,501 A * | 5/1996 | Tarlov | ................. 430/5 |
| 6,093,302 A | 7/2000 | Montgomery | |
| 6,197,503 B1 * | 3/2001 | Vo-Dinh et al. | .................... 435/6 |
| 6,280,595 B1 | 8/2001 | Montgomery | |
| 6,403,317 B1 * | 6/2002 | Anderson | .......................... 435/6 |
| 6,551,784 B2 | 4/2003 | Fodor et al. | |
| 6,605,796 B2 | 8/2003 | Brandinger et al. | |
| 6,794,052 B2 | 9/2004 | Schultz et al. | |
| 6,860,939 B2 * | 3/2005 | Hartzell | ........................... 117/43 |
| 6,985,655 B2 | 1/2006 | Yamamoto | |
| 7,125,451 B2 | 10/2006 | Hartzell | |

(Continued)

FOREIGN PATENT DOCUMENTS

JP 3447055 4/2003

(Continued)

OTHER PUBLICATIONS

McGall, et al., Jun. 4, 1997, *Journal of the American Chemical Society*, 119(22).

(Continued)

*Primary Examiner* — Sally Sakelaris
(74) *Attorney, Agent, or Firm* — David C. Ripma, Esq.; Jon M. Dickinson, Esq.

(57) ABSTRACT

A pixel-by-pixel, digitally-addressable, pixelated, precursor, fluid-assay, active-matrix micro-structure including plural pixels formed preferably on a glass or plastic substrate, wherein each pixel, formed utilizing low-temperature TFT and Si technology, includes (a) at least one non-functionalized, digitally-addressable assay sensor, and (b), disposed operatively adjacent this sensor, digitally-addressable and energizable electromagnetic field-creating structure which is selectively energizable to create, in the vicinity of the at least one assay sensor, an ambient electromagnetic field environment which is structured to assist in functionalizing, as a possession on said at least one assay sensor, at least one digitally-addressable assay site which will display an affinity for a selected fluid-assay material.

1 Claim, 5 Drawing Sheets

U.S. PATENT DOCUMENTS

| | | | |
|---|---|---|---|
| 7,128,783 | B2 | 10/2006 | Hartzell |
| 7,135,070 | B2 | 11/2006 | Hartzell |
| 7,156,916 | B2 | 1/2007 | Hartzell |
| 7,163,822 | B2 * | 1/2007 | Yazawa et al. ............. 435/287.2 |
| 2003/0035109 | A1 | 2/2003 | Hartwich et al. |
| 2003/0219196 | A1 * | 11/2003 | Weng et al. ..................... 385/17 |
| 2005/0063870 | A1 * | 3/2005 | Fukushima et al. ........ 422/82.05 |
| 2007/0072169 | A1 | 3/2007 | Peyvan et al. |
| 2008/0079663 | A1 * | 4/2008 | Hartzell et al. ................. 345/55 |

FOREIGN PATENT DOCUMENTS

| | | |
|---|---|---|
| JP | 2003-322613 | 11/2003 |
| JP | 2004-001200 | 8/2004 |
| JP | 2006-17706 | 1/2006 |
| JP | 2006-504111 | 2/2006 |
| WO | WO 9210092 | 6/1992 |

OTHER PUBLICATIONS

Arntz et al. 2003. "Label-free protein assay based on a nanomechanical cantilever array." *Nanotechnology*. 14:86-90 (5 pp).

Jacobson et al. 1985. "Functionalized Congeners of Adenosine: Preparation of Analogues with High Affinity for $A_1$-Adenosine Receptors" *J. Med. Chem.* 28:1341 (1 p, abstract only).

USPTO Office Action, U.S. Appl. No. 11/827,173, dated Nov. 27, 2009, 14 pages total.

USPTO Office Action, U.S. Appl. No. 11/827,173, dated May 21, 2010, 9 pages total.

USPTO Office Action, U.S. Appl. No. 11/827,173, dated Dec. 8, 2010, 10 pages total.

USPTO Office Action, U.S. Appl. No. 11/827,175, dated Jan. 3, 2011, 13 pages total.

USPTO Office Action, U.S. Appl. No. 11/827,174, dated Dec. 3, 2010, 14 pages total.

USPTO Office Action, U.S. Appl. No. 11/827,176, dated Jan. 3, 2011, 14 pages total.

USPTO Office Action, U.S. Appl. No. 11/888,491, dated Jun. 25, 2010, 11 pages total.

USPTO Office Action, U.S. Appl. No. 11/888,491, dated Nov. 15, 2010, 8 pages total.

Noda et al. "Development of Photolithography System with Liquid Crystal Device as Active Mask for Synthesizing DNA Chips", Proceedings of the Japan Society of Mechanical Engineers, Kanto Branch, the Japan Society for Precision Engineering, Ibaraki Conference, 2003, vol. 2003, p. 201-202. Japan.

USPTO Office Action, U.S. Appl. No. 11/827,173, dated Apr. 8, 2011, 11 pages total.

USPTO Office Action, U.S. Appl. No. 11/827,175, dated May 31, 2011, 11 pages total.

USPTO Office Action, U.S. Appl. No. 11/827,174, dated Apr. 11, 2011, 14 pages total.

USPTO Office Action, U.S. Appl. No. 11/827,176, dated May 31, 2011, 10 pages total.

USPTO Office Action, U.S. Appl. No. 11/888,491, dated Apr. 12, 2011, 11 pages total.

* cited by examiner

MICRO-PIXELATED FLUID-ASSAY PRECURSOR STRUCTURE

CROSS REFERENCE TO RELATED APPLICATION

This application claims filing-date priority to currently U.S. Provisional Patent Application Ser. No. 60/849,875, filed Oct. 6, 2006, for "Micro-Pixelated Array Assay Structure and Methodology". The entire disclosure content of that prior-filed provisional case is hereby incorporated herein by reference.

BACKGROUND AND SUMMARY OF THE INVENTION

This invention relates to a pixelated, thin-film-based, fluid-assay, active-matrix structure, and more particularly to a row-and-column micro-structure of active, individually digitally-addressable pixels which have been prepared on a supporting substrate as "blank slates" for later, selective, assay-specific, assay-site affinity functionalization, also referred to as pixel functionalization, to enable the performance of at least one kind of a fluid-material assay. This micro-structure is also referred to herein as an assay-affinity-lacking micro-structure, in which each pixel is spoken of as possessing an assay-affinity-lacking sensor, as will be explained hereinbelow.

Preferably, the invention takes the form of a relatively inexpensive, consumer-level-affordable, thin-film-based assay structure which features a low-cost substrate that will readily accommodate low-cost, and preferably "low-temperature-condition", fabrication thereon of substrate-supported matrix-pixel "components". "Low temperature" is defined herein as a being a characteristic of processing that can be done on substrate material having a transition temperature (Tg) which is less than about 850° C., i.e., less than a temperature which, if maintained during sustained material processing, would cause the subject material to lose dimensional stability. Accordingly, while the matrix-pixel technology of this invention, if so desired, can be implemented on more costly supporting silicon substrates, the preferred supporting substrate material is one made of lower-expense glass or plastic materials. The terms "glass" and "plastic" employed herein to describe a preferred substrate material should be understood to be referring also to other suitable "low-temperature materials Such substrate materials, while importantly contributing on one level to relatively low, over-all, end-product cost, also allow specially for the compatible employment, with respect to the fabrication of supported pixel structure, of processes and methods that are based on amorphous, micro-crystal and polysilicon thin-film-transistor (TFT) technology. In particular, these substrate materials uniquely accommodate the use of the just-mentioned TFT technology in such a way that electrical, mechanical and electromagnetic field-creating devices—devices that are included variously in the structure of the invention—can be fabricated simultaneously in a process flow which is consistent with the temperature tolerance of such substrate materials.

Regarding the preference herein for the use of low-temperature TFT technology, and briefly describing aspects of that technology, low-temperature TFT devices are formed through deposition processes that deposit silicon-based (or other-material-based, as mentioned below herein, and as referred to at certain points within this text with the expression "etc.") thin film semiconductor material (which, for certain applications, may, of course, later be laser crystallized). This is quite different from classic silicon CMOS device technology that utilizes a single-crystal silicon wafer bulk material as its semiconductor material. While the resulting TFT devices may not have the switching speed and drive capability of transistors formed on single-crystal substrates, TFT transistors can be fabricated cheaply with a relatively few number of process steps. Further, thin-film deposition processes permit TFT devices to be formed on alternate substrate materials, such as transparent glass substrates, for use, as an example, in liquid crystal displays. In this context, it will be understood that TFT device fabrication may variously involve the use typically of amorphous Si (a-Si), of microcrystalline Si, and or of polycrystalline Si formed by low-temperature internal crystalline-structure processing of amorphous Si. Such processing is described in U.S. Pat. No. 7,125,451 B2, the contents of which patent are hereby incorporated herein by reference.

For the sake simply of convenience of expression regarding the present invention, and in order to emphasize the "low-temperature" formation possibility which is associated with the invention in its preferred form, all aspects of assay-matrix pixel fabrication and resulting structure are referred to herein in the context and language of "low-temperature silicon on glass or plastic" construction, and also in the context and language of "low-temperature TFT and Si technology".

Returning now to a general description of the features of the present invention, a precursor pixel-matrix structure, which is formed utilizing the above-mentioned low-temperature TFT and Si technology, is provided preferably on a glass or plastic substrate, whereby, ultimately, and completely under the control of a recipient-user's selection, each pixel in that matrix is individually and independently affinity-functionalizable to display an affinity, i.e., an attraction, for at least one specific fluid-assay material, and following such functionalization, and the subsequent performance of a relevant assay, individually and independently digitally readable to assess assay results. The term "functionalization" herein, and each like term, means preparing a site within a pixel to possess an affinity, i.e., an attraction, for a particular fluid assay material.

The invention thus takes the form of an extremely versatile and relatively low-cost matrix assay precursor structure, also referred to herein interchangeably as a microstructure. It is a precursor structure in the sense that, as has just been mentioned above, it is not yet an assay-material-specific-functionalized assay structure, i.e., it is not yet assay-affinity functionalized, and until so functionalized, has no ability to attract any specific assay material. As will become apparent from the invention description which is provided herein, the structure of this invention is therefore one which is providable, as a singularity, to a user, in a special status which enables that user selectively to functionalize pixels in the structure, with great versatility, to perform one, or even plural different (as will be explained), type(s) of fluid-material assay (s).

While there are many ways in which the core characteristics of this invention may be visualized, one way of thinking about it is to recognize its analogy to those kinds of commercial products which are considered to be "staples" in commerce, i.e., base products which lie as key ingredients in a vast range of final products into which they are processed and incorporated. The structure of the present invention, in the context of its associated field of art and technology regarding the performances of fluid-material assays, is such a product. This analogy should clearly stand out as one reads the full description of the invention presented herein.

There is certain terminology, other than the "low-temperature" terminology defined above, which is employed in the description and characterization of this invention which should here be explained.

The concepts of, and terms relating to, "digital addressability" and "energizing" expressed herein are intended to refer to computer-controlled addressability and energizing.

The term "active-matrix" as used herein refers to a pixelated structure wherein each pixel is controlled by and in relation to some form of digitally-addressable electronic structure, which structure includes digitally-addressable electronic switching structure, defined by one or more electronic switching device(s), operatively associated, as will be seen, with also-included pixel-specific assay-sensor structure and pixel-bathing electromagnetic field-creating, or functionalizing, structure—all formed preferably by low-temperature TFT and Si technology as mentioned above.

The term "bi-alternate" refers to a possible matrix condition enabled by the present invention, wherein every other pixel in each row and column of pixels may selectively become commonly functionalized for one, specific type of a fluid-material assay. This condition effectively creates, across the entire area of the overall matrix of the invention, two differently functionalizable submatrices of pixels (what can be thought of as a two-assay, single-overall-matrix condition).

The term "tri-alternate" refers to a similar condition, but one wherein every third pixel in each row and column may selectively become commonly functionalized for one, specific type of a fluid-material assay. This condition effectively creates, across the entire area of the overall matrix, three, differently functionalizable submatrices of pixels (what can be thought of as a three-assay, single-overall-matrix condition). Individual digital addressability of each pixel permits these and other kinds of matrix-distributed functionalization options, if desired.

Other kinds of submatrices are, of course, possible, and one other type of submatrix arrangement is specifically mentioned hereinbelow. Whenever a user elects to employ a submatrix functionalization approach regarding an overall matrix made in accordance with the present invention, that approach may be employed to enable either (a) several, successive same-assay-material matrix-assay uses with the same overall matrix, or (b) several successive different-assay-material submatrix-assay uses also employing the same overall matrix.

It should be apparent that the use of a submatrix functionalization approach with respect to the matrix structure of the present invention enables a user to elect to perform selected assays at different pixel-distribution "granularities".

With respect to the concept of assay-site functionalization, except for the special features enabled by practice of the present invention that relate (a) to "pixel-specific" functionalization capability, and (b) functionalization under the "control" of a "digitally energized and character-managed", "assay-site-bathing" ambient electromagnetic field of a selected nature, assay-site functionalization is in all other respects essentially conventional in practice. Such functionalization is, therefore, insofar as its conventional aspects are concerned, well known to those generally skilled in the relevant art, and not elaborated herein, but for a brief mention later herein noting the probable collaborative use, in many functionalization procedures, of conventional flow-cell assay-sensor-functional processes.

While ultimately-enabled functionalization specificity, i.e., assay-affinity specificity for a particular selected assay site (resident within a given pixel), in accordance with practice of the present invention in certain instances, is generally and largely controlled by ambient "bathing" of that site with selected-nature electromagnetic-field energy received from an invention-prepared, digitally-energized, appropriately positionally located electromagnetic field-creating subcomponent, it turns out that site-precision specificity is not a critical operational factor. In other words, it is entirely appropriate if the entirety of a pixel becomes ultimately affinity "functionalized". Accordingly, various terminology referring to pixel functionalization and to assay-site functionalization is used herein interchangeably.

Each prepared "precursor" pixel, which is an active-matrix pixel as that language is employed herein, includes, as was mentioned, at least one, digitally-addressable, assay-affinity-lacking sensor which is designed to possess, or host, at least one ultimately to-be-functionalized fluid-assay site that will have and display an affinity for a selected, specific fluid-assay material. Each such assay site, in its non-functionalized, precursor condition, is referred to herein variously as a non-affinity-functionalized, or non-assay-functionalized, assay site. In its functionalized state, it is referred to variously as an affinity-functionalized assay site, as an assay-functionalized assay site, and as an affinity assay site. Each such pixel also includes, as earlier indicated, an "on-board", digitally-addressable, assay-site-bathing (also referred to as "pixel-bathing"), electromagnetic-field-creating structure (part of a thin-film electronic switching structure) which, among other things, is controllably energizable, as will be explained, (a) to assist in the affinity-functionalizing of such an assay site for the performance of a specific kind of fluid-material assay, and (b) to assist (where appropriate) in the output reading of the result of a particular assay. This field-creating structure, which, in terms of its functionalizing capability, is also referred to as an affinity functionalizer, and as an affinity-establishing functionalizer, is capable, via the inclusion therein of suitable, different, field-creating subcomponents, and in accordance with the present invention, of producing, as an ambient, pixel-bathing field environment within its respective, associated pixel, any one or more of (a) a light field, (b) a heat field, and (c) a non-uniform electrical field.

The invention, as suggested above, thus offers an extremely flexibly employable, staple-like, pixelated, precursor, fluid-assay, active-matrix structure, or micro-structure, wherein the individual pixels are not initially pre-ordained to function responsively with any specific fluid-assay material, but rather are poised with a readiness to have their respective, associated assay sensors later user-functionalized to respond with specificity to such an assay material.

In the proposed row-and-column arrangement of precursor assay pixels prepared in accordance with the practice of the present invention, each pixel includes a least one, and may include more than one, assay sensor(s), with each such assay sensor being ultimately functionalizable to host, or possess, at least one, but optionally and selectively plural, assay-material-specific assay sites that are functionalized appropriately for such materials.

Additionally, and with respect to the important and striking versatility which is offered by the present invention, and thinking about the concept generally mentioned above regarding submatrices, it is entirely possible for a user of the subject precursor structure of this invention to create plural, different unified areas (i.e., unified lower-pixel-count submatrices defined by next-adjacent, side-by-side pixels) within the overall, entire matrix structure which have their respective submatrix pixels functionalized to respond to a specific type of fluid-assay material, with each such different submatrix area being capable of responding to respective, different assay materials.

It should be understood that while the structure of the present invention, as will become apparent, is built in such a fashion that all addressable field-creating subcomponents within each pixel are remotely digitally addressable to assist in pixel functionalization, actual overall functionalization of an assay site on a pixel assay sensor may involve, additionally, as mentioned briefly earlier, the utilization of conventional flow-cell processes in order to implement a full correct functionalization procedure. For example, where an assay site in such a pixel is to become functionalized to respond in a DNA-type assay, conventional flow-cell technology may be used, in cooperation with functionalization assistance provided by the on-board field-creating structure, to carry out such full assay-site functionalization.

As will become apparent, one especially interesting feature of this invention is that it introduces the possibility of deriving assay-result data, including kinetic assay-reaction data, effectively along plural, special axes not enabled by prior art devices. For example, and with respect to the performance, or performances, of a selected, particular type of fluid-material assay, pixels in a group included in full matrix, or in a smaller-pixel-count submatrix, may be functionalized for assay use utilizing plural different levels, or intensities, of functionalization-assist fields, such as intensity-differentiated heat and/or non-uniform electrical fields. Such differentiated field-intensity functionalization can yield, following an assay, information regarding how an assay's results are affected by such "field-differentiated" pixel functionalization. Similarly, assay results may be observed by reading pixel output responses successively under different (changed) ambient field conditions that are then presented as "bathing" fields seriatim to information-outputting pixels.

Further in relation to the versatile utility of the present invention following user-pixel-functionalization and the performance of a relevant assay, and with respect specifically to the reading-out of completed-assay response information, time-axis output data may easily be gathered on a pixel-by-pixel basis via pixel-specific, digital output sampling.

Regarding the making of a precursor matrix micro-structure as proposed by the present invention, an important point to note is that the processes, procedures and methodologies which are employed specifically to fabricate this precursor structure may be drawn entirely from now-conventional micro-array fabrication practices, such as the earlier-mentioned TFT, Si, low-temperature, and low-cost-substrate technology practices, well known to those generally skilled in the art. Accordingly, further details of these practices, which form no part of the present invention, are not set forth herein. Those generally skilled in the relevant art will understand, from a reading of the present specification text, taken along with the accompanying drawing figures, exactly how to practice the present invention, i.e., will be fully enabled by the disclosure material in this application to practice the invention in all of its unique facets.

The various features and advantages of the present invention, including those generally set forth above, will become more fully apparent as the description of the invention which now follows below in detail is read in conjunction with the accompanying drawings.

DETAILED DESCRIPTION OF THE INVENTION

Figure 1:
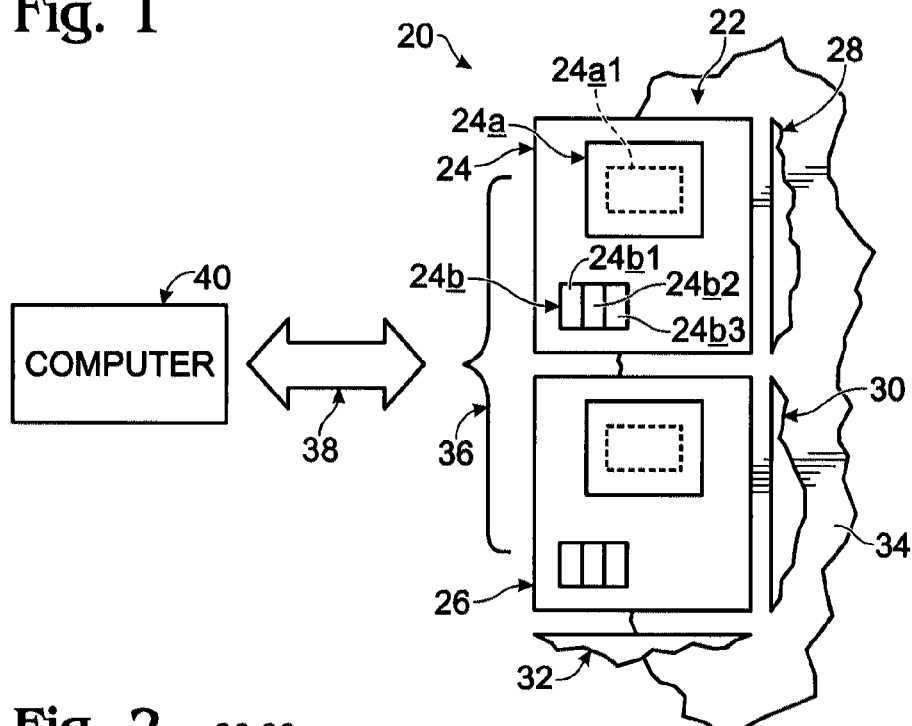
FIG. 1 is a simplified, fragmentary, block/schematic view of a portion of a digitally-addressable, pixelated, fluid-assay, active-matrix micro-structure formed in accordance with a preferred and best mode embodiment of the present invention. The pixels in this micro-structure are in precursor conditions—not yet functionalized to possess an affinity for any particular fluid assay material.
Figure 2:
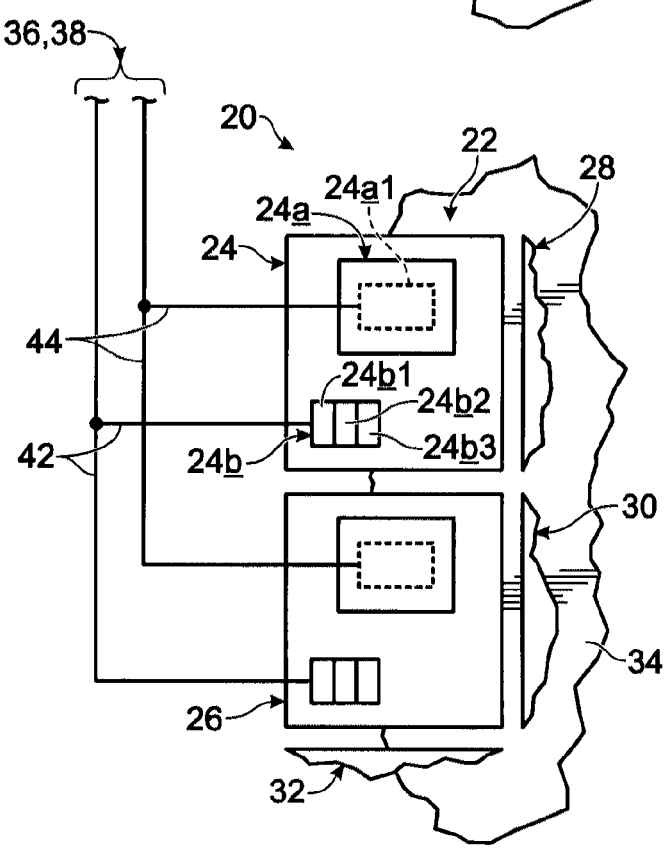
FIG. 2 is similar to FIG. 1, except that it provides a slightly more detailed view of the structure shown in FIG. 1.

Turning attention now to the drawings, and beginning with FIGS. 1 and 2, indicated generally at 20 is a fragmentary portion of a digitally-addressable, pixelated, fluid-assay, active-matrix micro-structure, referred to also as an assay-affinity-lacking micro-structure, which takes the form herein of a column-and-row array 22 of plural, individually externally addressable micro-pixels, or pixels, such as those shown at 24, 26, 28, 30, 32, formed, as will shortly be described, on an appropriate supporting, conventional-material, preferably glass or plastic, substrate 34. For the purpose of illustration herein, substrate 34 will be considered to be a glass substrate. These pixels include assay sensors which have not yet been functionalized to possess an affinity for any particular fluid assay material. Such sensors are referred to herein as assay-affinity-lacking sensors.

As was mentioned earlier herein, the specific low-cost and low-temperature methodologies and practices which are, or may be, utilized, in detail, to create the overall structure illustrated in FIGS. 1 and 2 are entirely conventional in nature, are well understood by those generally skilled in the relevant art, and thus may easily be practiced in well-known manners to produce the various structural aspects of micro-structure 20. For example, conventional Si-based, thin-film TFT patterning practices, such as well-known photolithographic practices, may be employed in ways that are familiar to those generally skilled in the art. Additionally, and for certain structures present in micro-structure 20, a low-temperature internal crystalline-structure processing approach may be employed to create certain desired mechanical characteristics, such as the bending characteristics of a cantilever beam like that pictured in FIG. 7, or a collection of material spikes like that shown in FIGS. 8-10C, inclusive. As was mentioned earlier, such internal crystalline-structure processing methodology is fully described in herein-incorporated U.S. Pat. No. 7,125,451 B2.

In the practice of the present invention, various non-critical dimensions may be chosen, for example, to define the overall lateral size of a micro-structure, such as micro-structure 20. Also, the number of pixels organized into the relevant, illustrated, overall row-and-column matrix may readily be chosen by one practicing the present invention. As an example, a micro-structure, such as micro-structure 20, might have lateral dimensions lying in a range of about 0.4×0.4-inches to about 2×2-inches, and might include an equal row-and-column array of pixels including a total pixel count lying in a range of about 100 to about 10,000. These size and pixel-count considerations are freely choosable by a practicer of the present invention.

Continuing with a description of what is shown in FIGS. 1 and 2, a bracket 36 and a double-headed, broad arrow 38 (see FIG. 1) represent an appropriate communication/addressing connection, or path, between pixels in micro-structure 20 and a suitable digital computer, such as the computer shown in block form in FIG. 1 at 40. Such a path exists under circumstances where a micro-structure, such as micro-structure 20, is being (a) functionalized, i.e., made assay-ready with affinity for at least one type of fluid assay material, or (b) "read" after the performance of a fluid-material assay. The pictured inclusion of computer 40 in FIG. 1 has been done to help illustrate and describe the completed-micro-structure utility of the present invention.

Regarding the illustrated, operative presence of a digital computer, such as computer 40, it should be understood that such a computer, while "remote and external" with respect to the internal structures of the pixels, per se, might actually be formed directly on-board substrate 34, or might truly be external to this substrate. In this context, it should be clearly understood that computer presence and/or location are not any part of the present invention.

In the particular preferred and best mode embodiment of micro-structure 20 which is illustrated in FIGS. 1 and 2, each of the mentioned precursor pixels is essentially identical to each other pixel, although, as will later be explained herein, this is not a necessary requirement of the present invention. This "not-necessary" statement regarding the characteristics of the present invention is based upon a clear understanding that there are various end-result fluid-assay applications with respect to which appropriately differentiated precursor pixels might be fabricated in a single, micro-structure array. Some of these differentiated-pixel concepts will be discussed more fully later herein.

In general terms, and using pixel 24 as an illustration to explain the basic construction of each of the pixels shown in array 22, included in pixel 24 are several, fully integrated, pixel-specific components, or substructures. These include, as part of more broadly inclusive pixel-specific electronic structure, (1) thin-film, digitally-addressable electronic switching structure, (2) a non-functionalized, precursor, individually remotely digitally-addressable and accessible assay sensor 24a (of the character generally mentioned above) which hosts a prospective, functionalizable, but not yet assay-affinity-ready, assay site $24a_1$, and (3) what is referred to herein as a pixel-bathing, ambient, environmental, electromagnetic-field-creating structure, or affinity-establishing functionalizer, 24b. Field-creating structure 24b, which is also remotely, or externally, individually digitally-addressable and accessible, and which can be thought of as forming at least a portion of a thin-film, electronic switching structure, is constructed to create, when energized, any one or more of three different kinds of assay-site-bathing, pixel-bathing, ambient, environmental electromagnetic fields in the vicinity of sensor 24a, including a light field, a heat field, and a non-uniform electrical field. While structure 24b, as was just mentioned, may be constructed to create one or more of these three different kinds of fields, in the micro-structure pictured in FIGS. 1 and 2, field-creating structure 24b has been designed with three field-creating subcomponents $24b_1$, $24_{22}$ and $24b_3$. Any one or more of these subcomponents may be energized to create, within pixel 24, an associated, ambient, pixel-bathing field condition. Subcomponent $24b_1$ is capable of creating an ambient pixel-bathing light field, subcomponent $24b_2$ an ambient pixel-bathing heat field, and subcomponent $24b_3$ an ambient pixel-bathing non-uniform electrical field. More will be said about these three different kinds of field-creating subcomponents shortly.

The use of a bathing electromagnetic field of an appropriate selected character during pixel functionalization, understood by those skilled in the art, and typically used with a functionalizing flow-cell process under way, operates to create, within a pixel and adjacent an assay site, an ambient environmental condition wherein relevant chemical, biochemical, etc. reactions regarding functionalization flow material can take place, at least at the prepared, sensor-possessed assay site, or sites, to ensure proper functionalization at that site. Such functionalization is referred to herein as establishing, as a presence on a sensor, an affinity assay site. A "prepared assay site" might typically, i.e., conventionally, be defined by a sensor borne area of plated gold.

Given the active-matrix nature of the micro-structure of the present invention, it should be understood at this point that each pixel is appropriately prepared with one or more conventional electronic switching device(s) (part of the mentioned electronic switching structure) relevant to accessing and addressing its included sensor and assay site, and to energizing its included field-creating structure. Illustrations of such devices are given later herein.

Looking for a moment specifically at FIG. 2, indicated generally at 42, 44 are two, different communication line systems which are operatively connected, respectively, to the field-creating structures in the illustrated pixels, and to the assay sensors and assay sites shown in these pixels. The upper, fragmented ends of line systems 42, 44 in FIG. 2 are embraced by a bracket marked with the two reference numerals 36, 38, which bracket represents the previously mentioned "path" of operative connection shown to exist in FIG. 1 between micro-structure 20 and computer 40. Line system 42 is utilized by such a computer to energize field-creating subcomponents during a functionalization procedure, and also to energize these same field-creating subcomponents, where appropriate, during a reading-out of the results of a performed assay. Line system 44 directly couples to computer 40, on a pixel-by-pixel basis, assay output responses derived from ultimately functionalized assay sites.

Figure 3:
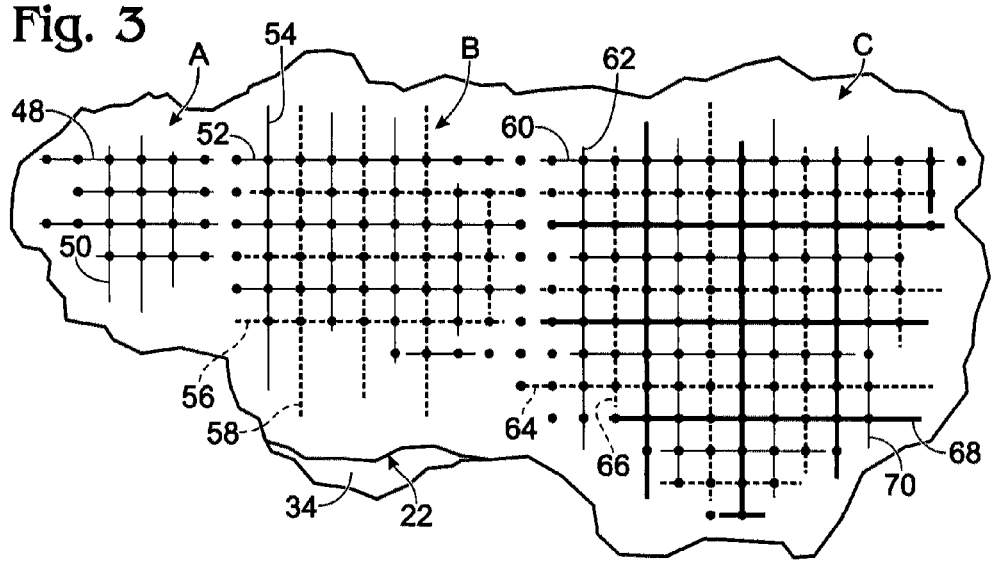
FIG. 3, which is prepared on a somewhat larger scale than those scales employed in FIGS. 1 and 2, illustrates, schematically, different, single, overall, matrix-organizational ways in which precursor fluid-assay pixels in the matrix micro-structure of this invention may be organized, user-selectively, into different functionalized arrangements for different fluid-assays that are ultimately to be performed.

Having thus now described generally the arrangement and makeup of the micro-structure of this invention with respect to how that structure is illustrated in FIGS. 1 and 2, we now shift attention to FIG. 3 in the drawings, which illustrates several different ways in which functionalized pixels, such as the pixels in array 22, may be organized and even differentiated in the hands of a user who is provided with a precursor structure made in accordance with this invention. To begin with, the obvious, large dots, which appear throughout in a row-and-column arrangement in FIG. 3, represent the locations of full-matrix next-adjacent pixels prepared in accordance with practice of this invention. One way of visualizing utilization of the invention, with regard to the entirety of this array of pixel-representing "dots", is to recognize that every pixel thus represented by the mentioned dots may be commonly functionalized to respond to a single, specific fluid-assay material.

By way of distinctions, specifically different regions A, B, C marked in FIG. 3 illustrate three other, representative, possible pixel functionalization patterns (specifically submatrix patterns) accommodated by the utility of the present invention.

In region A, which is but a small, or partial, region, or patch, of the overall matrix array 22 of pixels, a functionalized submatrix pattern has been created, as illustrated by solid, horizontal and vertical intersecting lines, such as lines 48, 50, respectively, including rows and columns of next-adjacent pixels, which pixels are all commonly functionalized for one particular fluid-material assay. With this kind of an arrangement, different patches, or fragmentary overall-matrix areas, of next-adjacent pixels may be differently functionalized so that a single, overall matrix array can be used in respective relations to these kinds of patch submatrices to perform plural, different, fluid-material assays.

In region B, intersecting, solid, horizontal and vertical lines, such as lines 52, 54, respectively, and intersecting, dashed, horizontal and vertical lines, such as lines 56, 58, respectively, illustrate two, different submatrix functionalization patterns which fit each into the category mentioned earlier herein as a "bi-alternate" functionalization pattern which effectively creates two, large-area-distribution submatrices within the overall matrix array 22 of pixels. These two pixel submatrices are distributed across the entire area of the overall matrix array, and are characterized by rows and columns of pixels which "sit" two pixel spacings away from one another.

Fig. C illustrates another submatrix functionalization pattern wherein intersecting, light, solid, horizontal and vertical lines, such as lines 60, 62, respectively, intersecting dashed, horizontal and vertical lines, such as lines 64, 66, respectively, and intersecting, thickened, solid, horizontal and vertical lines, such as lines 68, 70, respectively, represent what was referred to herein earlier as a "tri-alternate" functionalization arrangement distributed over the entire matrix array 22 of pixels—effectively dividing that array into three overlapping submatrices.

Those skilled in the art, looking at the illustrative, suggested functionalization patterns pictured in FIG. 3, will understand how these, and perhaps other, functionalization patterns interestingly tap the utility of the precursor structure of the present invention. In point of fact, what is shown in FIG. 3 suggests that the precursor structure of this invention offers a large, generous palette of opportunities for employing the micro-structure of this invention.

Figure 4:
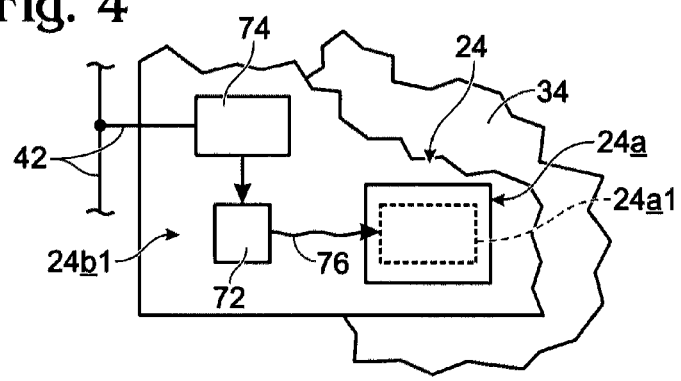
FIG. 4 is a fragmentary, block/schematic diagram illustrating one form of an electromagnetic field-creating structure prepared in accordance with practice of the present invention, and specifically such a structure which is intended to create an ambient, electromagnetic, pixel-bathing field environment characterized by light.
Figure 5:
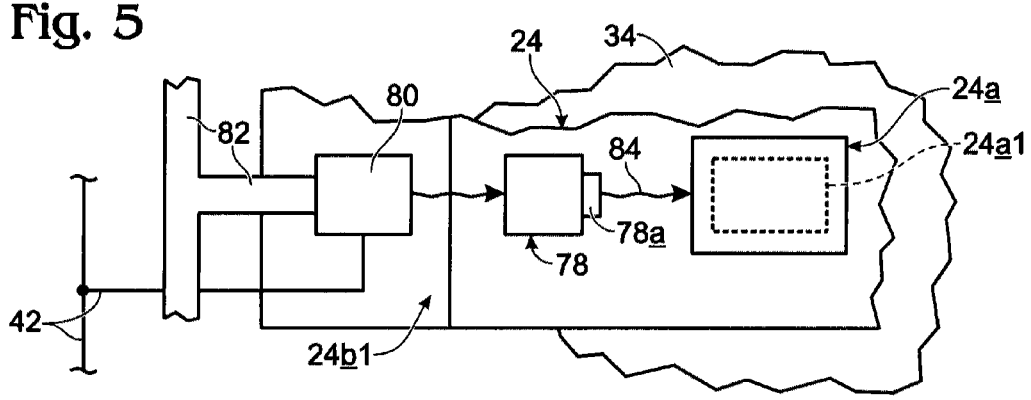
FIG. 5 is similar to FIG. 4, except that it illustrates another field-of-light-environment-creating structure.

Turning attention now to FIGS. 4 and 5, these two figures illustrate, schematically and fragmentarily, two different kinds of light-field-creating subcomponents. These illustrated subcomponents, with respect to what has been shown and discussed earlier herein regarding FIGS. 1 and 2, might sit at the field-creating subcomponent location which is labeled $24b_1$ in FIGS. 1 and 2. FIGS. 4 and 5, in relation to the appearances of things in FIGS. 1 and 2, have been drawn somewhat differently for illustration purposes.

Thus, shown specifically in FIG. 4 is an energizable, optical medium 72 which is energized/switched directly by the operation of a thin-film control transistor (an electronic switching device) shown in block form at 74. This control transistor has an operative connection to previously mentioned line system 42. A sinuous arrow 76 extends from medium 72 toward prospective assay site $24a_1$ which is hosted on sensor 24a. Arrow 76 schematically pictures the creation of a pixel-bathing field of light in the vicinity of site $24a_1$.

In FIG. 5, an optical beam device 78, having a light output port 78a, is switched on and off by means of an optical switching device 80 (an electronic switching device) which is fed light through an appropriate optical beam structure 82 which in turn is coupled to an off-pixel source of light. Switching of optical switching device 80 is performed by a computer, such as previously mentioned computer 40, and via the communication path provided by previously mentioned line system 42. A sinuous arrow 84 represents a path of light flow to create a pixel-bathing field of light in the vicinity of prospective assay site $24a_1$.

Figure 6:
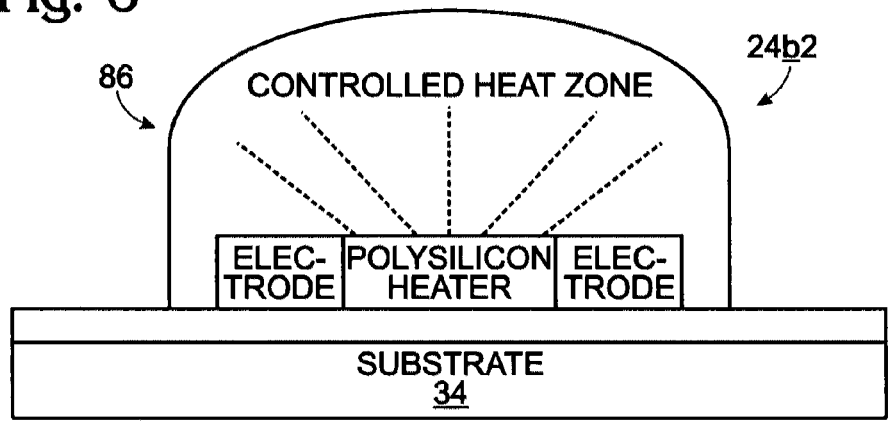
FIG. 6 provides a fragmentary, schematic illustration of one form of a heat-field-creating structure.

In each of the possible optical field-creating structures shown in FIGS. 5 and 6, there are different specific arrangements of optical media, well-known to those skilled in the art, which may be employed therein. For example, one such medium might have a horizontal-style configuration, and another arrangement might be characterized by a vertical-style arrangement. Such arrangements are well-known and understood by those skilled in the relevant art.

Figure 7:
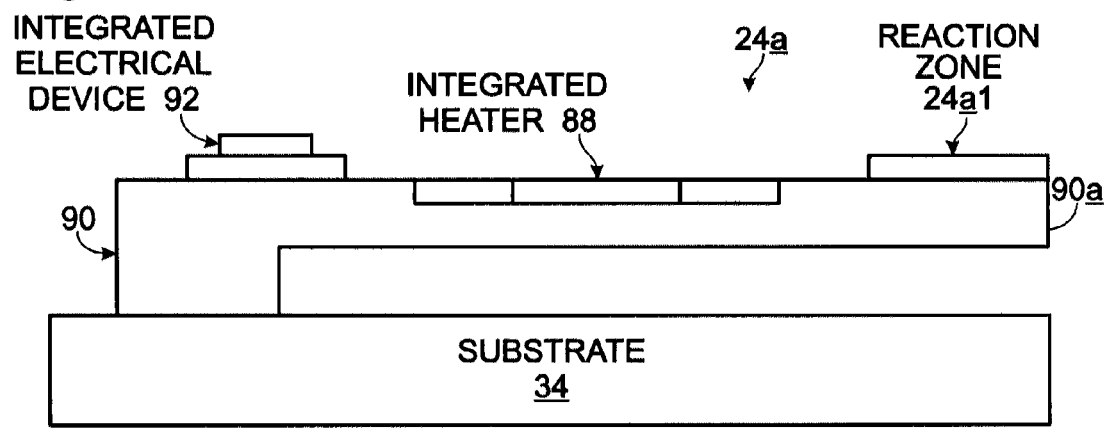
FIG. 7 illustrates fragmentarily another form of a heat-field-creating structure which has been prepared on the body of a mechanical cantilever beam which also carries an electrical signaling structure that responds to beam deflection to produce a related electrical output signal.

Directing attention now to FIGS. 6 and 7, here there are illustrated, schematically, two different, electronically switchable heat-field-creating subcomponents, one of which, namely that one which is pictured in FIG. 6, may be used at the location designated $24b_2$ in FIG. 1, and the other of which, namely that one which is shown in FIG. 7, may be used at the location of an on-sensor-24a site 88 which is shown only in FIG. 7. Entirely conventional and well-known, or recently introduced (see above-referred-to U.S. Pat. No. 7,125,451 B2 with regard to portions of the structure shown in FIG. 7), processes may be employed to produce the switchable heat-field-creating subcomponents illustrated in these two figures.

The first-mentioned version of a heat-field-creating subcomponent is shown generally at 86 in FIG. 6. This subcomponent (86) is also labeled $24b_2$ (in FIG. 6) in order to indicate its relationship to what has already been discussed above regarding the illustrations provided in FIGS. 1 and 2. From a brief look at the schematic illustration presented in FIG. 6, those generally skilled in the relevant art will easily recognize how to fabricate an appropriate, similar heat-field-creating organization. Accordingly, and because of the fact that many different, particular heat-field-creating arrangements may be employed, no specific details for such an arrangement are described or illustrated herein.

The pixel-bathing, heat-field-creating subcomponent version illustrated generally at 88 in FIG. 7 is one which is shown as having been formed directly adjacent prospective assay site $24a_1$ on a portion of assay sensor 24a, and specifically, formed directly on the beam 90a of a cantilever-type microdeflection device 90 whose basic material body has been formed utilizing the process mentioned above referred to as internal crystalline-structure processing.

Also formed on beam 90a is an electrical signaling structure 92 which may take the form of any suitable electrical device that responds to bending in beam 90a to produce a related electrical output signal which may be coupled from the relevant pixel ultimately to an external computer, such as computer 40.

Directing attention now to FIGS. 8-10C, inclusive, these figures illustrate various aspects of an electronically switchable, pixel-bathing, non-uniform-electrical-field-creating structure 94 which may be created within a pixel, such as within pixel 24 at the site shown at $24b_3$ in FIGS. 1 and 2. The mechanical spike structures seen in these figures have been fabricated employing the crystalline-structure-processing methodology described in the above-referred-to '451 B2 U.S. Patent.

Figure 8:
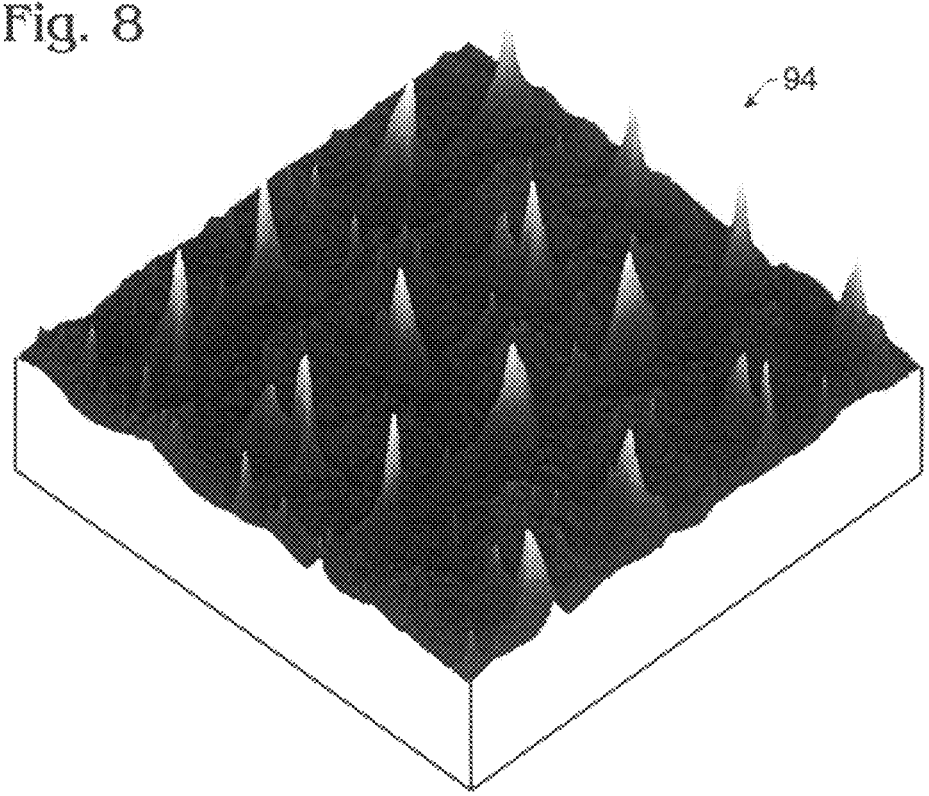
FIG. 8 is an isometric view of a pixel-bathing, non-uniform electrical-field-creating structure prepared through a recently developed process, touched upon later in this specification, involving internal crystalline-structure processing of substrate material.
Figure 9:
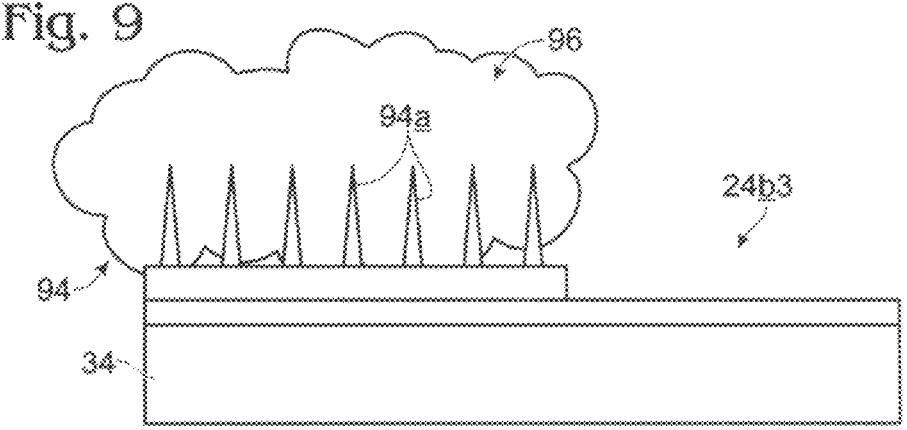
FIG. 9 provides a simplified side elevation of the structure presented in FIG. 8, schematically picturing, also, a pixel-bathing, non-uniform electrical field.

As can be seen in FIGS. 8 and 9, the structure suggested herein for the creation of a pixel-bathing non-uniform electrical field takes the form of a sub-array of very slender, approximately equal-height micro-spikes, such as those shown at 94a in FIG. 9, with regard to which electrical energization, as by a computer, such as computer 40, results in the production of an appropriate, pixel-bathing non-uniform electrical field, shown generally and very schematically in a cloud-like fashion at 96 in FIG. 9.

Figure 10A:
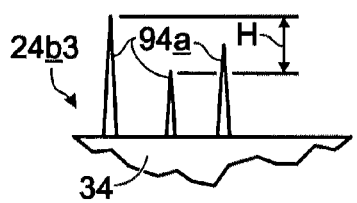
FIGS. 10A, 10B and 10C illustrate, in greatly simplified forms, three different kinds of three-dimensional spike features which may be created in relation to what is shown generally in FIGS. 8 and 9 for the production of a non-uniform electrical field.
Figure 10B:
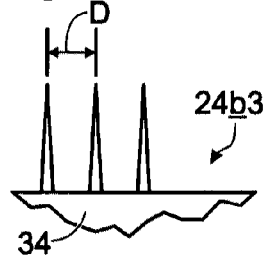
Figure 10C:
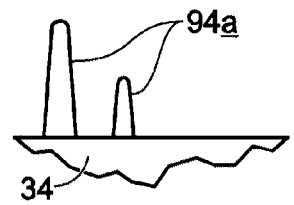

FIGS. 10A, 10B and 10C illustrate several, different, representative micro-spike configurations and arrangements which might be used to characterize a non-uniform electrical field-creating subcomponent. Such micro-spikes are simply illustrative of one of various kinds of different, electronically switchable structures which may be created within a field-creating structure in a pixel to develop, when energized, a suitable, pixel-bathing non-uniform electrical field.

FIG. 10A illustrates modified micro-spike structures 94a regarding which distributed micro-spikes may have, either uniformly, or differentially, different heights lying within a user-selectable height range generally indicated at H.

FIG. 10B illustrates an arrangement wherein micro-spikes 94a are configured like those shown in FIGS. 8 and 9, except for the fact that these FIG. 10B micro-spikes are more densely organized, as indicated by next-adjacent, interspike distance D. Such an interspike distance is freely chooseable by a user, and need not be uniform throughout a full sub-array of micro-spikes.

What is illustrated in FIG. 10C is an arrangement wherein the pictured micro-spikes 94a may have several differentiating characteristics, such as differentiating heights and sharpnesses, i.e., pointednesses.

Those skilled in the art will understand that the specific configuration of a non-uniform-electrical-field-creating subcomponent utilizing spikes, such as those just discussed, may be created in any one of a number of different ways.

Figure 11:
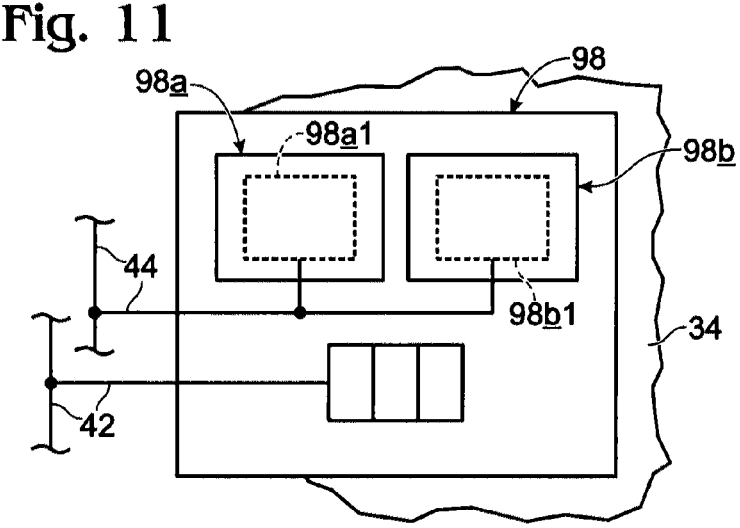
FIG. 11 provides a fragmentary view, somewhat like that presented in FIG. 1, but here showing a pixel which has been created in accordance with practice of the present invention to include two (plural) assay sensors, each of which is designed to receive and host a single, potential fluid-material assay site.
Figure 12:
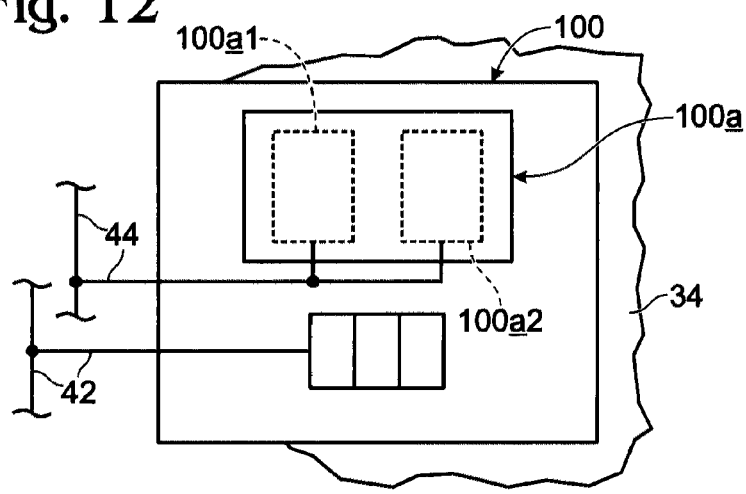
FIG. 12 is somewhat similar to FIG. 11, except that this figure shows a pixel which has been prepared in accordance with practice of the present invention to include a single fluid-assay sensor which possesses, or hosts, two (plural) potential fluid-material assay sites.

Addressing attention now to FIGS. 11 and 12, what is shown in FIG. 11 is a modified fragmentary region drawn from the fragmentary illustration of FIG. 1. This figure specifically illustrates a pixel 98 possessing two assay sensors 98a, 98b, each of which hosts but a single prospective assay site $98a_1$, $98b_1$, respectively.

The modification illustrated in FIG. 12 shows an arrangement wherein a pixel 100 which possesses a single sensor 100a is structured so as to host two, different, potential assay sites $100a_1$ and $100a_2$.

Thus, according to the present invention, a unique, precursor ("blank-slate-style"), pixelated active matrix, useable ultimately in a fluid-material assay, has been illustrated and described. This matrix has a structure whereby, ultimately, and completely under the control of a matrix-recipient-user's selection, each pixel in that matrix is individually and independently functionalizable to display an affinity for at least one specific fluid-assay material, and following such functionalization, and the subsequent performance of a relevant assay, individually and independently digitally readable to assess assay results.

The matrix structure of the invention utilizes a low-cost substrate material, such as glass or plastic, and features the low-temperature fabrication on such a substrate of supported pixel structures, including certain kinds of special internal components or substructures, all formed preferably by low-temperature TFT and Si technology as discussed above.

The matrix of the invention has the characteristics of a "staple" in commerce—a key factor which contributes to its special versatility with respect to how it can freely be functionalized in many ways by a user for employment in a fluid-material assay. Independent digital addressability of each pixel introduces interesting opportunities (not offered by prior art structures) for preparing to conduct, and ultimately conducting, such assays in many new ways, including ways that include examining assay results on kinetic and time-based axes of information. Depending upon how user-performed pixel functionalization is done, a single matrix may be employed in one-to-many fluid-material assays.

Accordingly, while a preferred and best mode embodiment of the invention, and certain modifications thereof, have been illustrated and described herein, additional variations and modifications may also be made which will come within proper spirit and scope of the invention.

We claim:

1. A non-functionalized, active-matrix, DNA-fluid-assay micro-structure comprising
    a single substrate having a surface, and
    disposed in common on that, surface, in the arrangement of a matrix array, plural, TFT-technology-fabricated pixels, each pixel including (a) a functionalizable assay site, and (b) disposed operatively and laterally adjacent each pixel's assay site, a control transistor, and an energizable optical medium operatively connected to, and energizable by operation of, the transistor, the optical medium being structured, when energized by operation of the transistor, to create from, and adjacent, its location on the substrate surface, and to bathe the associated, adjacent assay site with, an ambient light field which is operable to assist in performing subsequent DNA fluid-assay sensor probe creation on said site, thus to create a functionalized fluid-assay site.

* * * * *